United States Patent
Kuhn et al.

(10) Patent No.: US 11,006,049 B2
(45) Date of Patent: May 11, 2021

(54) VISUALIZATION MODULE AND METHOD FOR PRODUCING A VISUALIZATION MODULE

(71) Applicant: Scholly Fiberoptic GmbH, Denzlingen (DE)

(72) Inventors: Matthias Kuhn, Freiburg (DE); Maximilian Gotz, Freiburg (DE); Johannes Bourbon, Freiburg (DE); Stefan Schroer, Freiburg (DE); Holger Reinecke, Emmendingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 10 days.

(21) Appl. No.: 16/254,987

(22) Filed: Jan. 23, 2019

(65) Prior Publication Data

US 2019/0246027 A1    Aug. 8, 2019

(30) Foreign Application Priority Data

Feb. 6, 2018 (DE) .......................... 102018102587.4

(51) Int. Cl.
*A61B 1/07* (2006.01)
*H04N 5/235* (2006.01)
(Continued)

(52) U.S. Cl.
CPC ......... *H04N 5/2354* (2013.01); *A61B 1/0011* (2013.01); *A61B 1/051* (2013.01);
(Continued)

(58) Field of Classification Search
CPC ..... H04N 5/2354; A61B 1/0011; A61B 1/051; A61B 1/0607; A61B 1/0676;
(Continued)

(56) References Cited

U.S. PATENT DOCUMENTS

| 6,181,369 B1 | 1/2001 | Ooshima et al. |
| 2003/0171649 A1* | 9/2003 | Yokoi ...................... A61B 1/04 600/109 |

(Continued)

FOREIGN PATENT DOCUMENTS

| DE | 202009017097 | 3/2011 |
| DE | 102010012301 | 9/2011 |

(Continued)

OTHER PUBLICATIONS

WO 2011/116878 Machine Translation (Year: 2011).*

*Primary Examiner* — Nguyen T Truong
(74) *Attorney, Agent, or Firm* — Volpe Koenig

(57) ABSTRACT

A visualization module (1, 50, 100, 200), in particular for an endoscope (2), having an image sensor (3) and an illumination unit (4) for lighting a field of view of the image sensor (3), wherein the illumination unit (4) is arranged in the shadow of the image sensor (3) in the case of light that is incident perpendicularly on an end face (32) of the visualization module (1, 50, 100, 200), and the image sensor (3) and the illumination unit (4) are encapsulated at least partially in a transparent encapsulation material (5). A method for producing a visualization module (1, 50, 100, 200) is also provided.

20 Claims, 3 Drawing Sheets

(51) Int. Cl.
   *G03B 15/03*    (2021.01)
   *G02B 23/24*    (2006.01)
   *A61B 1/05*     (2006.01)
   *A61B 1/00*     (2006.01)
   *A61B 1/06*     (2006.01)
   *F21V 8/00*     (2006.01)
   *H04N 5/225*    (2006.01)

(52) U.S. Cl.
   CPC .......... *A61B 1/0607* (2013.01); *A61B 1/0676* (2013.01); *A61B 1/0684* (2013.01); *A61B 1/07* (2013.01); *G02B 23/2469* (2013.01); *G02B 23/2484* (2013.01); *G03B 15/03* (2013.01); *G02B 6/0006* (2013.01); *G03B 2215/0582* (2013.01); *H04N 2005/2255* (2013.01)

(58) Field of Classification Search
   CPC .... A61B 1/0684; A61B 1/07; G02B 23/2469; G02B 23/2484
   USPC .......................................................... 348/68
   See application file for complete search history.

(56) References Cited

U.S. PATENT DOCUMENTS

| | | |
|---|---|---|
| 2014/0107496 A1 | 4/2014 | Hellstrom et al. |
| 2014/0235942 A1 | 8/2014 | Hellstrom et al. |

FOREIGN PATENT DOCUMENTS

| | | | |
|---|---|---|---|
| DE | 102014208754 | 11/2015 | |
| WO | WO-2011116878 A2 * | 9/2011 | ............... A61B 1/05 |

* cited by examiner

VISUALIZATION MODULE AND METHOD FOR PRODUCING A VISUALIZATION MODULE

INCORPORATION BY REFERENCE

The following documents are incorporated herein by reference as if fully set forth: German Patent Application No. 10 2018 102 587.4, filed Feb. 6, 2018.

BACKGROUND

The invention relates to a visualization module having an image sensor and an illumination unit for lighting a field of view of the image sensor. The visualization module can be provided in particular for mounting in an endoscope. The invention furthermore also relates to a method for producing a visualization module.

Such visualization modules are already known and are placed in an endoscope shaft for example at a distal end of an endoscope. Such a visualization module can then be used to record an image of an object and/or of a cavity into which the visualization module was inserted, for example by inserting the endoscope into the cavity.

Until now, such visualization modules had to be produced with relatively great outlay in a plurality of assembly steps. For this reason, the associated production costs are also relatively high.

In addition, it is desirable in principle for the external dimensions of a visualization module transversely or perpendicularly to a recording direction of an image sensor to be as small as possible, with the image sensor generally being oriented transversely or perpendicularly to a longitudinal axis of the visualization module.

SUMMARY

The invention is therefore based on the object of providing an improved visualization module and a production method for a visualization module, wherein in particular a manufacturing outlay is to be reduced in order to provide a visualization module that meets the abovementioned requirements.

This object is achieved by a visualization module of the type mentioned in the introductory part having one or more features in accordance with the invention. Provided here is in particular a visualization module of the type mentioned in the introductory part, wherein the illumination unit is arranged in a shadow of the image sensor, and wherein the image sensor and the illumination unit are at least partially encapsulated in a transparent encapsulation material. This has the advantage that the external dimensions, that is to say the dimensions of the visualization module that extend transversely or perpendicularly to a recording direction and/or to a longitudinal axis of the visualization module, are as small as possible compared to previously known visualization modules.

The term "in the shadow" can mean here that the illumination unit is screened, in particular completely, by the image sensor as regards light that is incident perpendicularly in the visualization module, in particular at a distal end, such that the incident light is not incident on the illumination unit. The image sensor can therefore cast a shadow in the case of incident light, with the illumination unit being arranged in said shadow. Under a perpendicular angle of incidence of the incident light, the illumination unit in particular lies in the shadow of the image sensor and therefore receives no incident light. That means that the incident light is therefore also coming from a light source other than the illumination unit and/or the light is emitted at least by a surface outside the visualization module on which light from the illumination unit is incident. This may therefore in particular be a region over which rays which are extended beyond the image sensor, are incident thereon, and in particular extend parallel to the recording direction scan.

The encapsulation of the individual components of the visualization module can have the advantage that the visualization module can be finished without further assembly steps. That is to say, after the encapsulation it can be directly placed for example into an endoscope shaft and/or connected to an endoscope shaft to form a unit, in particular in one piece. It is consequently possible to be able to produce endoscopes with a relatively good recording quality in a particularly cost-effective manner.

The designation "distal end" can here relate to an end of the visualization module which faces away from a user during use and/or is located the furthest away. This is to say in particular the end by which the visualization module is insertable into a cavity.

The designation "proximal end" can here accordingly relate to an end of the visualization module which faces a user during use and/or is located the closest. The proximal end in particular can be remote from the distal end.

In accordance with a particularly advantageous development of the visualization module, provision may be made for a maximum external dimension of the visualization module to be defined by a maximum dimension of the image sensor. As already mentioned above, the maximum external dimension can be a maximum external dimension of the visualization module which extends transversely or perpendicularly to a recording direction, or to the recording direction already mentioned, and/or transversely or perpendicularly to a longitudinal axis, or to the longitudinal axis already mentioned, of the visualization module. The maximum external dimension can be in particular an external diameter of the visualization module. A maximum dimension of the image sensor can be defined in particular by a diagonal and/or a width and/or a height of the image sensor. This has the advantage that no installation space is required for the illumination unit in the visualization module by way of which a maximum external dimension, or the maximum external dimension, of the visualization module is defined.

According to a further advantageous refinement, a maximum external dimension of the illumination unit can be smaller than a maximum external dimension, or the maximum external dimension, of the image sensor. Alternatively, the maximum external dimensions of the illumination unit and of the image sensor can be the same. The maximum external dimension of the illumination unit can be a maximum external dimension of the illumination unit which extends transversely or perpendicularly to a recording direction, or to the recording direction already mentioned, and/or transversely or perpendicularly to a longitudinal axis of the visualization module, or to the longitudinal axis already mentioned, of the visualization module. In particular, the illumination unit can be arranged within a minimum cylinder which encloses the image sensor and is oriented parallel with respect to a recording direction, or the recording direction already mentioned, of the image sensor. The term "minimum" in this context can mean that the smallest possible diameter of the cylinder is selected to permit arrangement of the image sensor parallel to the cross-sectional area of the cylinder. The diameter of the cylinder preferably corresponds to a length and/or a width and/or a diagonal of the image sensor. Alternatively, the diameter can also correspond to the sum of a layer thickness of a web or two layer thicknesses of two webs and to a length and/or a width and/or a diagonal of the image sensor.

In order to be able to obtain a particularly compact design of the visualization module, provision may be made according to an advantageous development for the image sensor to be arranged closer to a distal end, in particular to the distal end already mentioned, of the visualization module than the illumination unit, and/or for the illumination unit to be arranged closer to a proximal end, in particular to the proximal end already mentioned, of the visualization module than the image sensor.

Alternatively or in addition, provision may be made in accordance with a further advantageous refinement for the image sensor to be arranged between a distal end, or the distal end already mentioned, and the illumination unit.

For the field of view of the visualization module to be able to be lit well so as to be able to attain a good recording quality, it is possible in accordance with a preferred refinement for light produced by the illumination unit to be guidable past the image sensor to the distal end of the visualization module using a light-guiding channel formed by the transparent encapsulation material.

In order to prevent recording disturbances by the image sensor, which could be caused for example by undesired influences of the illumination unit, the image sensor can be arranged outside an emission region of the illumination unit. The emission region can be preferably oriented here opposite to and/or transversely, in particular perpendicularly, to a recording direction, or to the recording direction already mentioned, of the image sensor. It is hereby more easily possible to prevent light signals coming directly from the illumination unit from being recorded by the image sensor. As a result, the recording quality of the image sensor can be significantly improved. With particular preference, the direction of the emission region of the illumination unit or the directions of the emission regions of the illumination units can deviate from the recording direction.

Alternatively or in addition, the illumination unit can be embodied as a light-emitting diode (LED) in accordance with an advantageous development. It is hereby possible to more easily prevent undesired heating of the visualization module by the illumination unit. In particular, by encapsulating the illumination unit which is preferably embodied in the form of an LED, waste heat that is being generated is better distributed.

In order that light, which is producible by the illumination unit, can be guided better to the distal end of the visualization module, it is possible in accordance with an advantageous development for the transparent encapsulation material to be surrounded externally at least partially by a reflective coating. The coating can thus exhibit a reflective surface. Targeted reflection can be achieved in this way. In other words, it may be possible for light, produced by the illumination unit, to be reflectable by the coating. It may be preferred here for the coating to be embodied at least partially on an inner side of an endoscope shaft or on an inner side of a sleeve or for the coating to at least partially be in contact with an inner side of an endoscope shaft or with an inner side of a sleeve. The light can also be reflected by a non-coated inner side of the sleeve. The sleeve can consequently have a reflective surface for example on its inner side.

It may be particularly advantageous if the encapsulation material exhibits an external mirroring means which forms a concave mirror for the illumination unit. This mirroring means can be realized for example by the previously mentioned coating. It may be particularly expedient here if the concave mirror is arranged at a proximal end, or at the proximal end already mentioned, of the visualization module. The concave mirror can preferably have a shape of a rotation paraboloid or a spherical shape. In this way, targeted reflection at the mirroring means and/or coating that forms an external boundary of the transparent encapsulation material is possible. In accordance with a particularly advantageous development, provision may furthermore be made for the illumination unit to be arranged in an interior space of the concave mirror and/or for the concave mirror to guide light from the illumination unit past the image sensor.

According to a preferred refinement, the visualization module can have an optical unit which, together with the image sensor and the illumination unit, is at least partially encapsulated by the transparent encapsulation material. The optical unit can have for example an optical lens or an optical lens system having a plurality of lenses. Alternatively or in addition, the optical unit can have at least one achromatic and/or aspheric lens. It may be particularly preferred here for the entire optical unit and the image sensor to have a matching outer contour, preferably for the optical unit to be embodied in the form of a cylinder.

In order to reduce the disturbing influence of stray light on the optical unit, the optical unit can have at least on one lateral surface a protective layer serving as a light shield and/or an in particular mechanically produced, thin-walled sleeve having a wall thickness of less than 50 µm. This sleeve could be reflective on its external surface for optimized output coupling of light. Alternatively or in addition, the transition region between the image sensor and the optical unit can have such a protective layer for providing improved shielding against stray light.

It may be preferred here for the optical unit and the image sensor to be combined into one camera module. In particular, the optical unit can be placed onto the image sensor and/or be connected thereto. Provision may therefore be made here for the optical unit together with the image sensor and the illumination unit to be at least partially encapsulated in the transparent encapsulation material.

In order to improve external stabilization of the visualization module, the visualization module can have a sleeve, or have the sleeve already mentioned, by which the transparent encapsulation material is enclosed on the outside at least partially, in particular at least a lateral surface of the encapsulation material. It is in particular possible hereby for stabilizing structures formed by the encapsulation material to be kept relatively narrow or be omitted so as not to widen, or widen only slightly, a maximum external dimension, or the maximum external dimension, of the visualization module by way of said stabilizing structures. The sleeve can therefore keep the individual encapsulated components of the visualization module better together in stabilizing fashion. The sleeve can therefore be used to better prevent a displacement of the individual components—i.e. in particular image sensor, illumination unit, transparent encapsulation material and/or optical unit—relative to one another.

In order to be better able to prevent light produced by the illumination unit from being incident directly on the image sensor, in particular at least one rear side of the image sensor, provision may be made in accordance with an advantageous development for the visualization module to have a reflection body. It may be particularly advantageous here if the reflection body is arranged in an optical path between the illumination unit and the image sensor, with the reflection body preventing light produced by the illumination unit from being incident on the image sensor, in particular being incident on a rear side of the image sensor.

It may here be further preferred for the reflection body to be arranged closer to a proximal end, or to the proximal end already mentioned, of the visualization module than the image sensor. It may be particularly expedient if the reflection body is arranged on a rear side of the image sensor and/or of a circuit carrier.

In order to improve targeted reflection of the light, which is incident on the reflection body, of the illumination unit past the image sensor, the reflection body can have a curved surface and/or a surface which is parabolic in cross section. The reflection body can preferably have a spherical shape or a paraboloid shape. The reflection body can also have a shape that is suitable for further passing on light.

In accordance with a further advantageous refinement of the visualization module, the illumination unit can be integrated in a reflection body, or in the reflection body. Alternatively, the illumination unit can also be arranged at a distance from the reflection body.

As an alternative to a reflection body, an absorption body may be provided. The design and arrangement of the absorption body can in principle correspond to the previously described reflection body. By using an absorption body, light that is incident thereon can be attenuated or nearly completely absorbed.

In order to obviate the need, for example in the case of a defect of a component of the visualization module that is encapsulated in the encapsulation material, to exchange a supply line together with the encapsulated components, an electrical connection of the illumination unit and/or of the image sensor can be guided entirely outside the transparent encapsulation material. The electrical connection of the illumination unit and/or of the image sensor can here be in the form for example of one or more supply lines and/or of a printed circuit board or a plurality of printed circuit boards. It can be particularly advantageous here if a flexible printed circuit board is provided. This has the advantage that the respective electrical connection has a relatively low weight and/or requires less installation space than for example cable connections. It is furthermore more easily possible to supply the illumination unit and the image sensor by way of a common electrical connection, independently of where they are arranged relative to one another, because the flexible printed circuit board is able to be bent particularly well.

In order to be able to protect the illumination unit particularly well against bumps and jolts, the illumination unit can be encapsulated completely in the transparent encapsulation material. This can mean in particular that all sides of the illumination unit are covered with encapsulation material.

Alternatively or in addition, it may be advantageous if an electrical connection, or the electrical connection already mentioned, of the illumination unit and/or of the image sensor is/are guided at least partially through the transparent encapsulation material.

The electrical connection of the illumination unit and/or of the image sensor can be in the form for example of a flexible and/or bendable printed circuit board. A particularly compact and relatively expedient refinement of the visualization module can be obtained for example by way of the illumination unit and/or the image sensor having a common electrical connection, in particular wherein only one electrical supply line and/or one printed circuit board for the illumination unit and the image sensor is required.

A high-quality refinement of the visualization module can be obtained by the transparent encapsulation material being pressed during the encapsulation from a distal end, or the distal end already mentioned, of the visualization module toward a proximal end, or the proximal end already mentioned, of the visualization module. A differentiation of the side from which encapsulation took place during fabrication of the visualization module can under certain circumstances be made with reference to a location of the injection points that formed in the process. In the visualization module, at least one injection point can therefore be formed at the distal end.

According to a further advantageous refinement of the visualization module, the visualization module can have a plurality of, in particular two, illumination units. The emission regions thereof can here be oriented in different directions. The emission regions of the illumination units can preferably be oriented transversely, in particular perpendicularly, and/or opposite to one another. With further preference, it may alternatively or in addition be the case that the emission regions overlap or do not overlap. Provision can furthermore alternatively or in addition be made for the illumination units to produce in each case light of a different wavelength and/or polarization.

According to an advantageous development, provision may be made for the image sensor to have a rectangular or a square base area, wherein the corners of the image sensor divide a light guide channel, or the light guide channel already mentioned, which is formed by the transparent encapsulation material, into a plurality of, in particular four, individual light guide channels. In this refinement, the smallest possible external dimensions of the visualization module can be attained, while very good lighting of the field of view is still possible.

To form structures stabilizing the cohesion of the encapsulated components, in each case a web having a layer thickness of less than 200 µm, in particular less than 100 µm, in particular less than 75 µm, preferably having a layer thickness of between 20 µm and 50 µm, can be formed between the corners and an external periphery of the transparent encapsulation material. In this case, a maximum dimension of the visualization module can thus additionally be defined in addition to a maximum dimension of the image sensor by way of the layer thickness of the webs. The maximum dimension of the visualization module can thus be defined by a sum of the maximum dimension of the image sensor and the layer thicknesses of two webs. If desired, it is possible in addition for a sleeve, or for the sleeve already mentioned, surrounding the encapsulated components to be provided, which means that a maximum external dimension of the visualization module is additionally defined by the wall thickness of the sleeve.

Provision may furthermore be made for the image sensor to be arranged on a printed circuit board, or on the printed circuit board already mentioned, which defines the widest dimension of the image sensor transversely or perpendicularly to a recording direction.

In order to attain a more exact orientation of the encapsulated components relative to one another, it is possible according to an advantageous development for the image sensor and the illumination unit to be arranged on a common circuit carrier, or on the common circuit carrier already mentioned. By using a circuit carrier, simpler positioning of the image sensor relative to the illumination unit is thus possible, because an orientation of the two components is already effected before the encapsulation with the encapsulation material is performed. Simpler manufacturing is consequently also possible, because a change in position of the image sensor and of the illumination unit relative to one another after or during the encapsulation with encapsulated material is no longer possible. In particular, the circuit carrier can be a printed circuit board, or can be the printed circuit board already mentioned. It may be preferred here for the image sensor and the illumination unit to be arranged on mutually opposite sides of the circuit carrier. In addition, it is even better possible due to the circuit carrier to prevent light produced by the illumination unit from striking the image sensor in an undesired manner because the circuit carrier may constitute an additional optical barrier between the image sensor and the illumination unit.

The visualization module described here is in particular especially well-suited for use for the production of an endoscope, in particular a single-use endoscope. This endoscope may preferably be a chip-in-tip (CIT, in short) endoscope. With further preference, the endoscope may be a medical endoscope.

The invention thus further relates to an endoscope having a visualization module, as is described and claimed in this document. This may preferably be a single-use endoscope, which may be discarded after a single use. In particular, it may be a CIT endoscope. With preference, the endoscope may be a medical endoscope. In order to improve the light guidance of the endoscope without increasing a maximum external dimension of the endoscope, it may be advantageous if the visualization module is enclosed by an endoscope shaft only partially, in particular at the proximal end. A cross-sectional diameter of the visualization module is here preferably matched to a cross-sectional diameter of an endoscope shaft, in particular in a manner such that the visualization module and the endoscope shaft have the same external diameter.

To achieve the abovementioned object, a method having one or more steps according to the invention is also provided. In particular, a method for producing a visualization module is provided here, comprising the steps of:

arranging an illumination unit in the shadow of an image sensor within an encapsulation mold, in particular by arranging the illumination unit and the image sensor on a circuit carrier, preferably on a circuit carrier that is in the form of a printed circuit board, and filling the cavities surrounding the illumination unit and the image sensor, in particular the camera module, with a transparent encapsulation material, preferably from a distal end of the visualization module to a proximal end of the visualization module.

The method described and claimed in this document is in particular especially well-suited for producing a visualization module, as is described and claimed in this document.

According to an advantageous development of the method, provision may be made for a plurality of injection points to be formed on an injection side of the encapsulation mold which are used to introduce the transparent encapsulation material into cavities which are to be filled and are separated from one another by the image sensor.

Alternatively or in addition, in accordance with an advantageous development of the method, provision can be made for a connection channel, which in particular encircles the image sensor, to be formed on the injection side of the encapsulation mold between the individual cavities to be filled.

In other words, the invention relates to a visualization module, in particular for an endoscope, having an image sensor and an illumination unit for lighting a field of view of the image sensor, wherein the illumination unit is arranged in the shadow of the image sensor in the case of light that is incident perpendicularly on an end face of the visualization module, and wherein the image sensor and the illumination unit are encapsulated at least partially in a transparent encapsulation material. The invention additionally relates to a method for producing a visualization module.

BRIEF DESCRIPTION OF THE DRAWINGS

Several exemplary embodiments of the invention will be described in more detail below with reference to the figures. The invention is however not restricted to these exemplary embodiments. Further exemplary embodiments result from the combination of the features of individual or a plurality of claims with one another and/or with individual or a plurality of features of the exemplary embodiments.

In partially highly schematic illustration.

DETAILED DESCRIPTION

Figure 1:
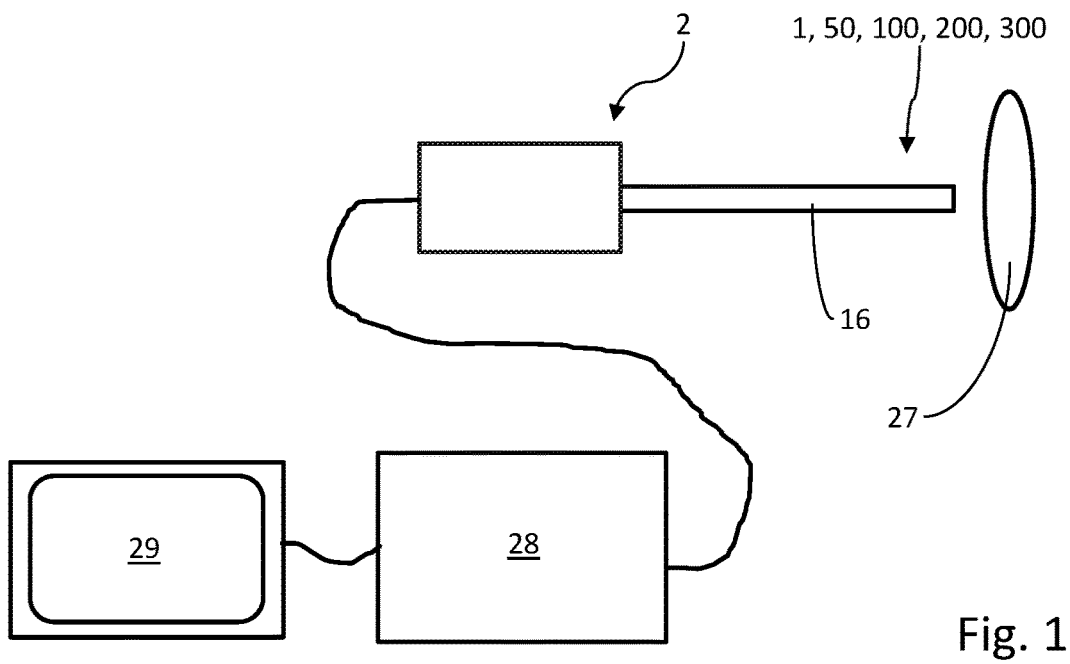
FIG. 1 shows an overall view of an embodiment of an endoscope according to the invention having a visualization module.

FIG. 1 shows an arrangement having an endoscope 2 with a visualization module 1, 50, 100, 200, 300. The endoscope 2 is here electrically connected to a CCU (camera control unit) 28 and a display unit 29.

FIGS. 2 to 6 show several exemplary embodiments of a visualization module 1, 50, 100, 200, wherein the different exemplary embodiments overall are in each case designated 1, 50, 100, 200 or 300.

The visualization module 1, 50, 100, 200, 300 generally has an image sensor 3 and an illumination unit 4. The illumination unit 4 can be embodied for example in the form of a light-emitting diode or a plurality of light-emitting diodes. The image sensor 3 and the illumination unit 4 are encapsulated at least partially in a transparent encapsulation material 5. The encapsulation material 5, from which an encapsulation material body is formed, can be for example a suitable plastic. In this way, particularly small dimensions compared to conventional visualization modules can be attained. In addition, the manufacturing costs can be significantly reduced because complicated post-processing steps are not necessary.

A maximum external dimension 6 of the visualization module 1, 50, 100, 200, 300, which extends in particular transversely or perpendicularly to a recording direction 7 and transversely or perpendicularly to a longitudinal axis 8 of the visualization module 1, 50, 100, 200, 300, is here determined by a maximum dimension of the image sensor 3. Depending on the shape of the image sensor 3, this may be for example a width 9, a height 10 and/or a diagonal 30 of the image sensor 3. The maximum external dimension 6 of the visualization module 1, 50, 100, 200 can be in particular an external diameter of the visualization module 1, 50, 100, 200, 300. The recording direction 7 can thus be directed parallel to the longitudinal axis 8 of the visualization module 1, 50, 100, 200, 300.

Figure 2:
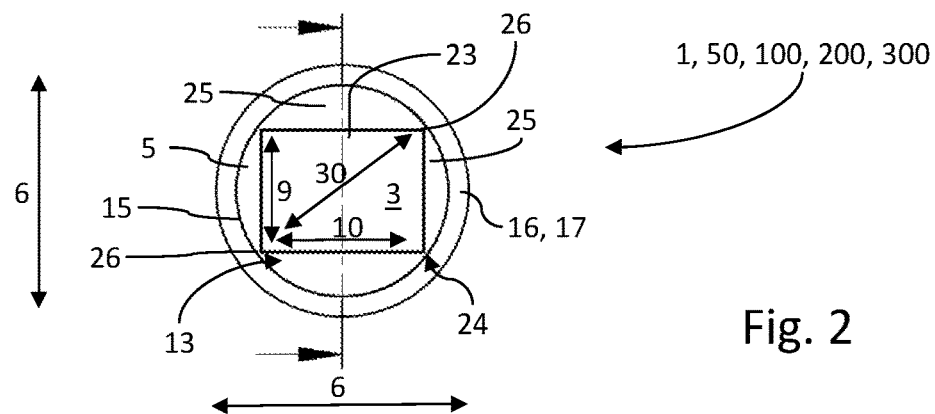
FIG. 2 shows a front view of a general embodiment of a visualization module according to the invention.

The visualization module 1, 50, 100, 200, 300 can have, in particular in the region in which the image sensor 3 is arranged, a circularly round cross section (cf. FIG. 2). As can be gathered from FIG. 2, the maximum external dimension 6 of the visualization module 1, 50, 100, 200, 300 in the embodiment shown in FIG. 2 is determined mainly by the diagonal 30 of the image sensor 3, because said diagonal 30 represents a maximum dimension of the image sensor (with the wall thickness of the sleeve 17 and the layer thickness of the webs 26 not being taken into account here because they are merely optional).

A rectangular base area 23 of the image sensor 3 is therefore likewise arranged perpendicularly to the recording direction 7 and/or perpendicularly to the longitudinal axis 8 of the visualization module 1, 50, 100, 200, 300.

A maximum dimension of the illumination unit 4, or of the illumination units 4, in all illustrated exemplary embodiments of the visualization module 1, 50, 100, 200, 300 is in each case smaller than the maximum dimension of the respective image sensor 3.

An at least partially cylindrical shape of the visualization module 1, 50, 100, 200, 300 is formed by the encapsulation material 5, in which the illumination unit 4 and the image sensor 3 are arranged one behind the other in the recording direction 7. The visualization module 1, 50, 100, 200, 300 can preferably taper toward the proximal end 12. With particular preference, the visualization module 1, 50, 100, 200, 300 has the shape of a bullet, because this shape is insertable particularly easily for example into an endoscope shaft 16.

In general terms, the illumination unit 4 in all exemplary embodiments is arranged in the shadow of the image sensor 3. That means that light that is incident from outside at a distal end 11 of the visualization module 1, 50, 100, 200, 300 strikes the image sensor, which consequently shields the illumination unit 4, which is arranged therebehind, from the incident light at a perpendicular angle of incidence of the incident light. An incidence direction 33 of the incident light therefore extends parallel to the longitudinal axis 8 and/or to the recording direction 7. Using the image sensor 3, a two-dimensional image of an object 27 can thus be recorded if light that is emitted by said object 27 strikes the image sensor 3.

A light guide channel 13 is formed by the transparent encapsulation material 5. The light guide channel 13 can be used to guide the light produced by the illumination unit 4 past the image sensor 3 so that it finally exits at the distal end 11 of the visualization module 1, 50, 100, 200, 300 to light a field of view of the image sensor 3. The image sensor 3 is consequently arranged between the illumination unit 4, or the illumination units 4, and the distal end 11 of the visualization module 1, 50, 100, 200, 300. In this way, the image sensor 3 is thus arranged further away from a proximal end 12 of the visualization module 1, 50, 100, 200, 300 than the at least one illumination unit 4.

The transparent encapsulation material 5 is surrounded on the outside by a reflective coating 15, with which the light produced by the illumination unit 4 is reflectable. This reflective coating 15 thus forms a concave mirror 34, in the interior of which the illumination unit 4 is arranged and which guides the light produced by it past the image sensor 3 to the front and/or outside. An end face 32 formed by the encapsulation material at the distal end 11 of the visualization module 1, 50, 100, 200, 300 has no such coating 15, which means it is free from any coating. Provision can, however, be made for the end face 32 to have microstructures for directing and/or focusing exiting light beams. The end face 32 thus corresponds to the exit region of the light produced by the illumination unit 4. Due to the coating 15, the produced light can thus be guided even more efficiently past the image sensor 3 and/or to the distal end 11 of the visualization module 1, 50, 100, 200, 300. The reflective coating 15 can at least partially be in contact with an inner side of a sleeve 17, which serves for stabilizing the components encapsulated by the encapsulation material 5. The sleeve 17 can here enclose at least a lateral surface of the cylinder. It is likewise conceivable for the visualization module 1, 50, 100, 200, 300 not to have a sleeve 17, wherein preferably the coating 15 in this case is in contact at least partially with an inner side of an endoscope shaft 16, for example of the endoscope 2 mentioned above.

In other words, the transparent encapsulation material 5 has a mirroring means arranged on the outside, which is omitted merely at the end face. At the proximal end 12 of the visualization module 1, 50, 100, 200, 300, the transparent encapsulation material 5 has a curved surface which can have a parabolic shape, for example, in cross section, as can be seen in FIGS. 3 to 6. The concave mirror 34, by way of which the light produced by the illumination unit 4 is reflectable, can be formed by said curved surface in combination with the previously mentioned reflective coating 15.

Figure 4:
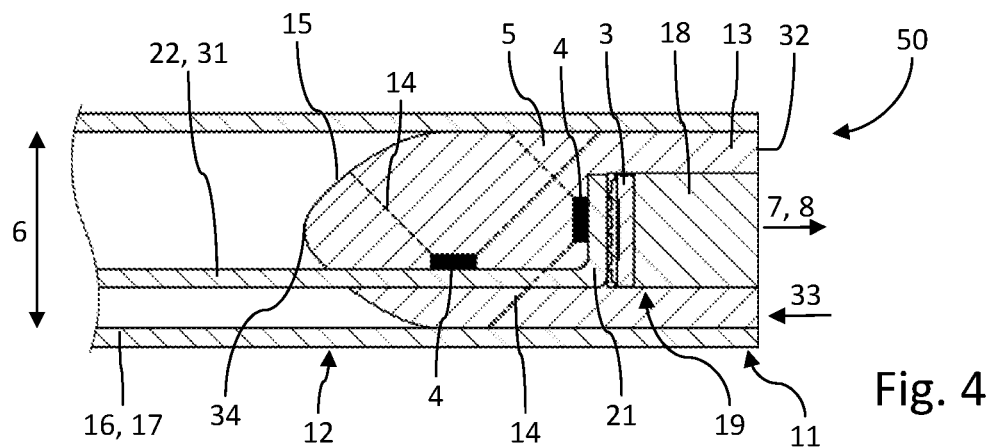
FIG. 4 shows a section illustration of an embodiment variant of the visualization module from FIG. 2, wherein the profile of the section in FIG. 2 is indicated by way of the line that is designated by the two arrows, wherein in this refinement of the visualization module, two illumination units are provided which are both encapsulated completely in encapsulation material, and wherein the emission regions of the illumination units partially overlap.
Figure 6:
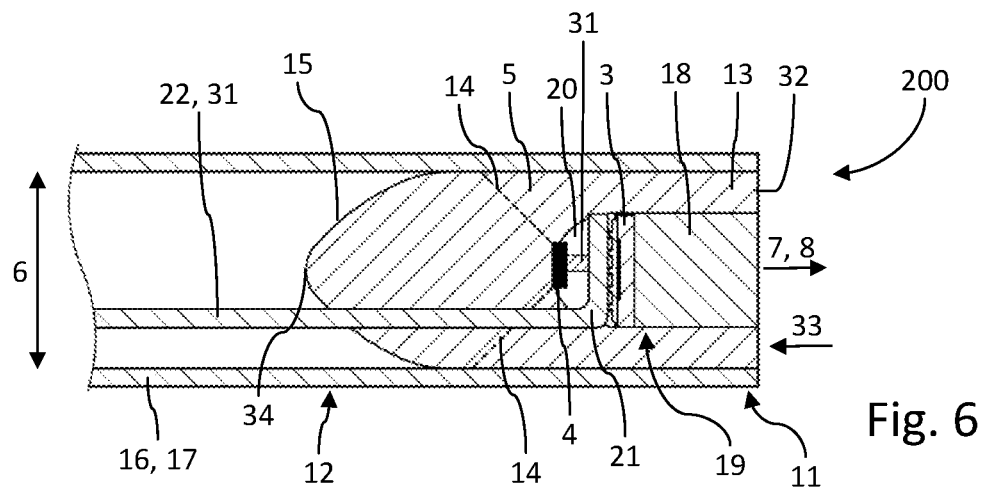
FIG. 6 shows a section illustration of an embodiment variant of the visualization module from FIG. 2, wherein the profile of the section in FIG. 2 is indicated by way of the line that is designated by the two arrows, wherein in this refinement of the visualization module, an illumination unit is provided which is completely encapsulated in encapsulation material, and wherein an electrical connection of the illumination unit is guided partially inside the encapsulation material.

An electrical connection 22 of the image sensor 3 and/or an electrical connection 31 of the illumination unit 4 can be realized for example by a circuit carrier 21, in the form of a printed circuit board, on which the image sensor 3 and the illumination unit 4 are arranged and/or to which the image sensor 3 and the illumination unit 4 are electrically connected. The illumination unit 4 can, as is shown in FIGS. 4 and 6, be arranged on a side of the circuit carrier 21 that faces away from the image sensor 3. The printed circuit board can preferably be flexible, which makes it particularly easy to arrange the printed circuit board within the available installation space in a space-saving manner.

In order to be able to better reach the illumination unit 4, that is to say in order to replace a defective illumination unit 4, for example, the latter can be left exposed at least in terms of its rear side in particular at the proximal end 12 of the visualization module 1, 50, 100, 200, 300. That means that the illumination unit 4 in this case is not completely surrounded by encapsulation material 5. It can be particularly advantageous here if the illumination unit 4 is designed such that it is able to be removed from the encapsulation material 5 and/or an electrical connection 31 of the illumination unit 4 is guided entirely outside the encapsulation material 5 to the illumination unit 4 (cf. FIG. 5). The illumination unit 4 can in this refinement therefore be placed in the previously mentioned concave mirror, for example. The electrical connection 31 of the illumination unit 4 can here branch off from an electrical main supply line, that is to say for example the previously mentioned printed circuit board.

The visualization module 1, 50, 100, 200, 300 furthermore has an optical unit 18. The optical unit 18 is likewise encapsulated in the transparent encapsulation material 5 together with the image sensor 3 and the illumination unit 4. In particular, the optical unit 18 has a cylindrical shape, wherein at least one lateral surface of the optical unit 18 extending parallel with respect to the longitudinal axis 8 is surrounded by encapsulation material 5.

The optical unit 18 can be present for example in the form of an optical lens or a plurality of optical lenses or have an optical lens or a plurality of optical lenses. In this case, said lens may be, for example, an achromatic lens. The lens or the lenses of the optical unit 18 can be curved in particular convexly and/or concavely. The optical unit 18 can be combined with the image sensor 3 to form a camera module 19. It may be expedient here if the image sensor 3 and the optical unit 18 are not displaceable relative to one another in terms of their position, that is to say are spatially fixed relative to one another. The embodiment of a camera module 19 which is surrounded by encapsulation material 5 together with the illumination unit 4 makes possible a particularly cost-effective manufacture of the visualization module 1, 50, 100, 200, 300. The optical unit 18 can have a flush transition to the end face 32 at the distal end 11.

The exemplary embodiments from FIGS. 3 to 6 differ in part in terms of their number of illumination units 4 and/or of the orientation of an emission region 14 of the illumination units 4.

Figure 5:
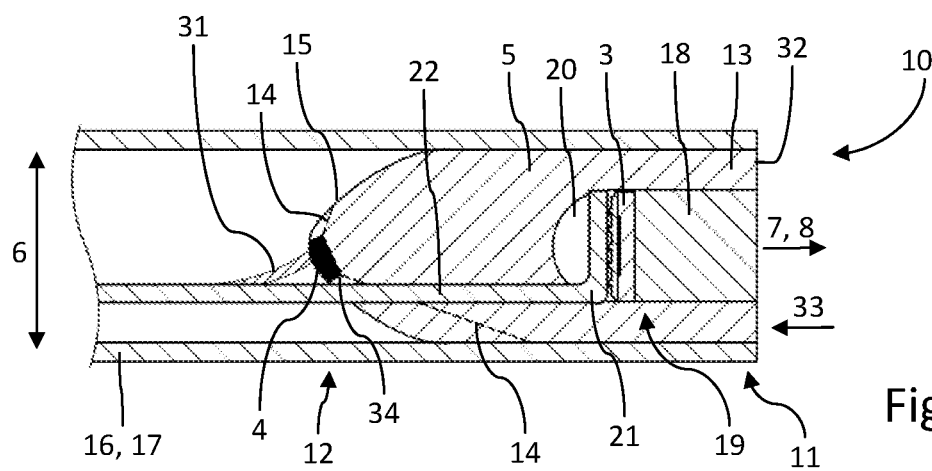
FIG. 5 shows a section illustration of an embodiment variant of the visualization module from FIG. 2, wherein the profile of the section in FIG. 2 is indicated by way of the line that is designated by the two arrows, wherein in this refinement of the visualization module, an illumination unit is provided, the rear side of which is not, or not completely, encapsulated in encapsulation material, and wherein an electrical connection of the illumination unit is guided completely outside the encapsulation material.

The visualization modules 100, 200 from FIGS. 5 and 6 additionally have a reflection body 20, which is arranged in each case in an optical path between the illumination unit 4 and the image sensor 3. The reflection body 20, however, is also combinable with the embodiment variants from FIGS. 3, 4 and 7 independently of the embodiments shown of the visualization module 1, 50, 100, 200, 300. The reflection body 20 is capable of preventing even more that the light produced by the illumination unit 4 strikes the image sensor 3, in particular a rear side of the image sensor 3. The reflection body 20 is thus arranged closer to a proximal end 12 of the visualization module 1, 50, 100, 200, 300 than the image sensor 3. The reflection body 20 can, as is shown in FIGS. 5 and 6, be arranged for example on a side of the circuit carrier 21 that faces away from the image sensor 3.

As is shown by the exemplary embodiment in FIG. 6, the illumination unit 4 can also be placed and/or integrated in the reflection body 20. An electrical connection 31 of the illumination unit 4 can in this case be guided through the reflection body 20. In particular, the electrical connection 31 of the illumination unit 4 can here branch off from the circuit carrier 21 already mentioned.

Figure 3:
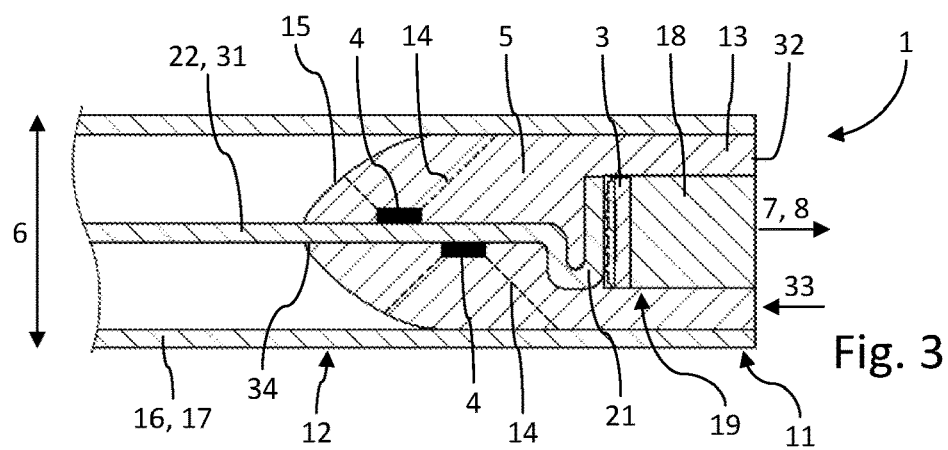
FIG. 3 shows a section illustration of an embodiment variant of the visualization module from FIG. 2, wherein the profile of the section in FIG. 2 is indicated by way of the line that is designated by the two arrows, wherein in this refinement of the visualization module, two illumination units are provided which are both encapsulated completely in encapsulation material, and wherein the emission regions of the illumination units are oriented in opposite directions.

FIG. 3 shows a variant having two illumination units 4, which are arranged on opposite sides of the already mentioned circuit carrier 21, which is provided in the form of a printed circuit board. The emission regions 14 of the two illumination units 4 therefore do not intersect, but are oriented in opposite directions. The emission regions 14 are additionally oriented perpendicularly to the already mentioned recording direction 7.

Further provision can be made in general for the illumination units 4 to be arranged such that they are offset along the longitudinal axis 8 and/or spaced apart from one another. It is likewise conceivable that, in one variant having a plurality of illumination units 4, the individual illumination units 4 produce light of a different wavelength, in particular a different color.

Figure 7:
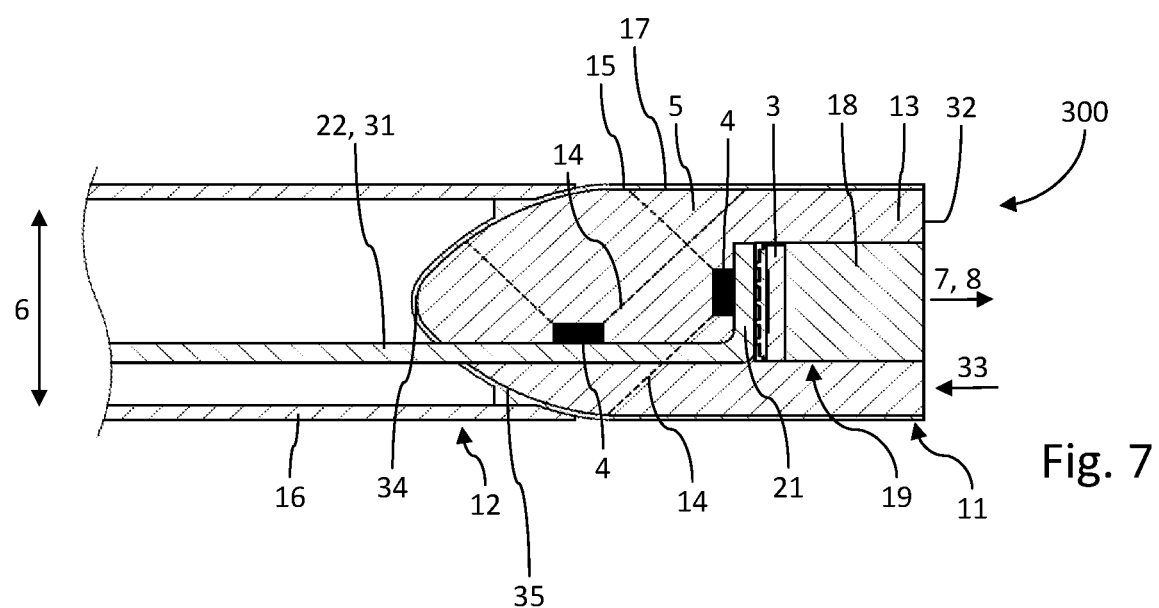
FIG. 7 shows a section illustration of an embodiment variant of the visualization module from FIG. 2, wherein the profile of the section in FIG. 2 is indicated by way of the line that is designated by the two arrows, wherein in this refinement of the visualization module, the transparent encapsulation material body is enclosed only partially by a sleeve and/or an endoscope shaft.

FIGS. 4 and 7 show further variants having two illumination units 4 each, which are arranged on the same side of the previously mentioned circuit carrier 21, which is provided in the form of a printed circuit board. The emission regions 14 of the two illumination units 4 here intersect, however, because they are oriented transversely or perpendicularly to one another. The emission region 14 of one of the two illumination units 4 is here oriented for example perpendicularly to the recording direction 7, and the emission region 14 of the other illumination unit 4 is oriented in the opposite direction of the recording direction 7.

The variants shown in FIGS. 5 and 6 each have one illumination unit 4. As can be seen in FIG. 5, the illumination unit 4 and/or its emission region 14 can be arranged at an angle, in particular at an acute angle, with respect to the longitudinal axis 8. However, it is further also possible for the illumination unit 4 and/or its emission region 14 to be oriented parallel with respect to the longitudinal axis 8 and/or in the direction opposite the recording direction 7, as is shown in FIG. 6.

The light guide channel 13 can be divided by the image sensor 3 into a plurality of individual light guide channels 25. In the variant shown in FIG. 2, four individual light guide channels 25 are formed. In this refinement variant, it may make sense if the previously described stabilizing sleeve 17 is provided so as to better be able to prevent widening of the individual light channels 25. In this case, the maximum external dimension 6 of the visualization module 1, 50, 100, 200, 300 is determined by the sum of the diagonal 30 of the image sensor 3 and/or a wall thickness of the sleeve 17.

What is special in the embodiment variant according to FIG. 7 is that the visualization module 300 is enclosed only partially by the endoscope shaft 16. The visualization module 300 has a reflective coating 15 at the side surfaces and/or is at least partially surrounded by a sleeve 17, with the light being reflectable at the inner side thereof. The visualization module 300 has a taper at its proximal end 12, via which the visualization module 300 is insertable or inserted into the endoscope shaft 16. The visualization module 300 can be connected to the endoscope shaft 16 by way of soldering and/or welding and/or adhesive bonding. So as to be able to secure the visualization module 300 in the endoscope shaft 16 such that it does not rotate and/or tilt, an encircling step 35 can be formed at the proximal end 12 of the visualization module 300, in particular on the reflective coating 15, said step 35 in its inserted state being in contact with the inner wall of the endoscope shaft 16 and defining the orientation of the visualization module 300. The step 35 thus serves for supporting and orienting the visualization module 300 at the endoscope shaft 16. Alternatively or in addition, however, other coupling elements and counter-coupling elements can also be formed on the endoscope shaft 16 and at the proximal end 12 of the visualization module 300, said elements making possible anti-rotation and/or anti-tilt holding of the visualization module 300 on the endoscope shaft 16. The embodiment variant according to FIG. 7 has the advantage that a cross section of the light guide channel 3 is enlarged, with the result that even better lighting of an object 27 is possible. The maximum external dimension 6 of the visualization module 300 can thus be determined in particular only by the diagonal 30 of the image sensor 3.

This has the advantage that even in an endoscope having such a visualization module 300 in the region of an endoscope tip, the maximum external dimension 6 of the endoscope is determined in particular only by the diagonal 30 of the image sensor 3 and in particular not by a wall thickness of the endoscope shaft 16. Preferably, a cross-section diameter of the visualization module 300 is matched to a cross-section diameter of an endoscope shaft 16. This creates a flush transition between the visualization module 300 and the endoscope shaft 16.

In order to be able to obtain a particularly stable construction of a visualization module 1, 50, 100, 200, 300, in which the use of the previously described stabilizing sleeve 17 could be omitted, if desired, it is possible for in each case a web 26 made of encapsulation material 5 having a layer thickness of less than 200 µm, in particular of less than 100 µm, in particular of less than 75 µm, preferably with a layer thickness between 20 µm and 50 µm, to be formed between the corners 24 of the rectangular base area 23 of the image sensor 3 and an outer periphery of the transparent encapsulation material 5. The stabilizing structures in the form of webs 26 made of encapsulation material 5 can therefore connect the individual light guide channels 25 to form a single, in particular encircling, light guide channel 13. At the same time they prevent, similar to the sleeve, a possible widening of the individual light guide channels 25. Due to the formation of the relatively narrow webs 26, it is additionally possible for a maximum external dimension 6 of the visualization module 1, 50, 100, 200, 300 to be kept especially small. Finally, in this embodiment variant, the maximum external dimension 6 of the visualization module 1, 50, 100, 200, 300 is defined by a sum of the layer thicknesses of two webs 26 and the diagonal 30 of the image sensor 3.

During the encapsulation of the individual components of the visualization module 1, 50, 100, 200, 300, the transparent encapsulation material 5 is pressed from the distal end 11 toward the proximal end 12 into an encapsulation mold in which the components were previously arranged.

In order to better prevent the components of the visualization module 1, 50, 100, 200, 300 to be encapsulated from shifting during an encapsulation process using transparent encapsulation material 5, it is possible for all components to be previously arranged on and secured to the circuit carrier 21 and for the encapsulation material 5 to subsequently be pressed into the encapsulation mold to fill the cavities around the image sensor 3 and the further components. The cavities can here be separated from one another in particular by the image sensor 3, or gaps are provided between the corners 24 of the image sensor 3 and an inner wall of the encapsulation mold, which gaps are entered by encapsulation material 5, forming the previously mentioned webs 26.

In order to make possible particularly uniform encapsulation, the encapsulation mold can have an encircling connection channel at one injection side of the encapsulation material 5. The individual cavities to be filled can be connected by said connection channel. A fill level of the encapsulation material 5 is therefore the same in all hollow bodies to be filled during an encapsulation process. This makes a particularly uniform filling of the cavities possible, resulting in a particularly high quality of the visualization module 1, 50, 100, 200, 300.

LIST OF REFERENCE SYMBOLS 1, 50, 100, 200, 300 visualization module
2 endoscope
3 image sensor
4 illumination unit
5 transparent encapsulation material
6 maximum external diameter of the visualization module
7 recording direction
8 longitudinal axis
9 width of the image sensor
10 height of the image sensor
11 distal end of the visualization module
12 proximal end of the visualization module
13 light guide channel
14 emission region
15 reflective coating
16 endoscope shaft
17 sleeve
18 optical unit
19 camera module
20 reflection body
21 circuit carrier
22 electronic connection of the image sensor
23 base area
24 corner of the image sensor
25 individual light guide channel
26 web
27 object to be recorded
28 CCU
39 display unit
30 diagonal
31 electrical connection of the illumination unit
32 end face
33 incidence direction of the incident light
34 concave mirror
35 step

The invention claimed is:

1. A visualization module (1, 50, 100, 200, 300), comprising:
   an image sensor (3),
   an illumination unit (4) that lights a field of view of the image sensor (3), the illumination unit (4) is arranged in a shadow of the image sensor (3), and
   a transparent encapsulation material (5) that forms a light guide channel (13) that is configured such that light produced by the illumination unit (4) in back of the image sensor (3) is guided by the light guide channel (13) past the image sensor (3) and out of the shadow of the image sensor (3) to a distal end (11) of the visualization module (1, 50, 100, 200, 300),
   wherein the transparent encapsulation material (5) at least partially encapsulates the image sensor (3) and the illumination unit (4) and forms one continuous block of material that extends from the illumination unit (4) around the image sensor (3) and to the distal end (11).

2. The visualization module (1, 50, 100, 200, 300) as claimed in claim 1, wherein a maximum external dimension (6) of the visualization module (1, 50, 100, 200, 300) extending at least one of perpendicularly to a recording direction (7) or perpendicularly to a longitudinal axis (8) of the visualization module (1, 50, 100, 200, 300), is defined by a maximum external dimension of the image sensor (3).

3. The visualization module (1, 50, 100, 200, 300) as claimed in claim 2, wherein the maximum external dimension of the image sensor (3) is at least one of a diagonal (30), a width (9), or a height (10) of the image sensor (3).

4. The visualization module (1, 50, 100, 200, 300) as claimed in claim 2, wherein a maximum external dimension of the illumination unit (4) is smaller than the maximum external dimension of the image sensor (3) or the maximum external dimensions of the illumination unit (4) and of the image sensor (3) are the same, such that the illumination unit (4) is arranged within a minimum cylinder which encloses the image sensor (3) and is oriented parallel with respect to the recording direction (7) of the image sensor (3).

5. The visualization module (1, 50, 100, 200, 300) as claimed in claim 1, wherein at least one of: (a) the image sensor (3) is arranged closer to a distal end (11) of the visualization module (1, 50, 100, 200, 300) than the illumination unit (4), (b) the illumination unit (4) is arranged closer to a proximal end (12) of the visualization module (1, 50, 100, 200, 300) than the image sensor (3), or (c) the image sensor (3) is arranged between the distal end (11) and the illumination unit (4).

6. The visualization module (1, 50, 100, 200, 300) as claimed in claim 1, wherein the image sensor (3) is arranged outside an emission region (14) of the illumination unit (4), with the emission region (14) being oriented at least one of counter to or transversely to a recording direction (7) of the image sensor (3).

7. The visualization module (1, 50, 100, 200, 300) as claimed in claim 1, wherein the illumination unit (4) comprises a light-emitting diode.

8. The visualization module (1, 50, 100, 200, 300) as claimed in claim 1, wherein the transparent encapsulation material (5) is at least partially enclosed on an outside with a reflective coating (15) such that light produced by the illumination unit (4) is reflectable by the coating (15), and the coating (15) is in contact at least partially with an inner side of an endoscope shaft (16) or is formed on or in contact with an inner side of a sleeve (17).

9. The visualization module (1, 50, 100, 200, 300) as claimed in claim 1, wherein the encapsulation material (5) has an external mirroring which forms a concave mirror for the illumination unit (4), and the illumination unit (4) is arranged in an interior of the concave mirror (34) and the concave mirror (34) guides light from the illumination unit (4) past the image sensor (3).

10. The visualization module (1, 50, 100, 200, 300) as claimed in claim 1, further comprising an optical unit (18), which, together with the image sensor (3) and the illumination unit (4) is at least partially encapsulated with the transparent encapsulation material (5), with the optical unit (18) and the image sensor (3) being combined to form a camera module (19), and a sleeve (17) that at least partially encloses the transparent encapsulation material (5) on an outside thereof.

11. The visualization module (1, 50, 100, 200, 300) as claimed in claim 1, further comprising at least one of a reflection body (20) or an absorption body arranged in an optical path between the illumination unit (4) and the image sensor (3), the at least one of the reflection body (20) or the absorption body being arranged closer to a proximal end (12) of the visualization module (1, 50, 100, 200, 300) than the image sensor (3), and the at least one of the reflection body (20) or the absorption body is arranged on a rear side of at least one of the image sensor (3) or a circuit carrier (21), and the at least one of the reflection body (20) or the absorption body has a curved surface in cross-section.

12. The visualization module (1, 50, 100, 200, 300) as claimed in claim 11, wherein the illumination unit (4) is integrated in the at least one of the reflection body (20) or the absorption body, and an electrical connection (22, 31) of at least one of the illumination unit (4) or the image sensor (3) is guided completely outside the transparent encapsulation material (5).

13. The visualization module (1, 50, 100, 200, 300) as claimed in claim 1, wherein the illumination unit (4) is encapsulated completely in the transparent encapsulation material (5) and an electrical connection (22, 31) of at least one of the illumination unit (4) or the image sensor (3) is guided at least partially through the transparent encapsulation material (5).

14. The visualization module (1, 50, 100, 200, 300) as claimed in claim 1, wherein the transparent encapsulation material (5) is pressed during the encapsulation from a distal end (11) of the visualization module (1, 50, 100, 200, 300) in a direction of a proximal end (12) of the visualization module (1, 50, 100, 200, 300).

15. The visualization module (1, 50, 100, 200, 300) as claimed in claim 1, wherein the illumination unit comprises a plurality of illumination units (4), with emission regions (14) thereof being oriented in different directions, and the illumination units (4) each produce light having at least one of a different wavelength or polarization.

16. The visualization module (1, 50, 100, 200, 300) as claimed in claim 1, wherein the image sensor (3) and the illumination unit (4) are arranged on a common circuit carrier (21) comprising a printed circuit board, with the image sensor (3) and the illumination unit (4) being arranged on mutually opposite sides of the common circuit carrier (21).

17. An endoscope (2) comprising a visualization module (1, 50, 100, 200, 300) as claimed in claim 1, an endoscope shaft (16) in which the visualization module (1, 50, 100, 200, 300) is at least partially arranged, and a cross-sectional diameter of the visualization module (1, 50, 100, 200, 300) is matched to a cross-sectional diameter of the endoscope shaft (16).

18. A method for producing a visualization module (1, 50, 100, 200, 300), comprising:
arranging an illumination unit (4) in a shadow of an image sensor (3) within an encapsulation mold, by arranging the illumination unit (4) and the image sensor (3) on a circuit carrier (21), and
filling cavities surrounding the illumination unit (4) and the image sensor (3) with a transparent encapsulation material (5), from a distal end (11) of the visualization module (1, 50, 100, 200, 300) to a proximal end (12) of the visualization module (1, 50, 100, 200),
such that the transparent encapsulation material (5) forms a light guide channel (13) and light produced by the illumination unit (4) in back of the image sensor (3) is guided by the light guide channel (13) past the image sensor (3) and out of the shadow of the image sensor (3) to the distal end (11) of the visualization module (1, 50, 100, 200, 300), and
wherein
the transparent encapsulation material (5) at least partially encapsulates the image sensor (3) and the illumination unit (4) forming one continuous block of material (5)

extending from the illumination unit (4) around the image sensor (3) and to the distal end (11).

19. The method as claimed in claim 18, further comprising
- forming a plurality of injection points on an injection side of the encapsulation mold,
- introducing the transparent encapsulation material (5) using the injection ports into cavities which are to be filled and are separated from one another by the image sensor (3), and
- forming a connection channel which encircles the image sensor (3) on the injection side of the encapsulation mold between the individual cavities to be filled.

20. A visualization module (1, 50, 100, 200, 300) comprising:
- an image sensor (3) that has a rectangular or square base area (23), wherein corners (24) of the image sensor (3) divide a light guide channel (13), formed by a transparent encapsulation material (5), into a plurality of individual light guide channels (25), and
- in each case a web (26) having a layer thickness of less than 200 µm is formed between the corners (24) and an outer periphery of the transparent encapsulation material (5), and wherein the image sensor (3) is arranged on a circuit carrier (21) that defines a widest dimension of the image sensor (3) transversely or perpendicularly to a recording direction (7).

* * * * *